United States Patent [19]

Isono et al.

[11] 4,400,070

[45] Aug. 23, 1983

[54] FOCUS DETECTING DEVICE FOR OPTHALMOLOGIC INSTRUMENTS

[75] Inventors: Masaru Isono; Kazuo Nunokawa; Masayuki Kondo; Shinzo Takada, all of Tokyo, Japan

[73] Assignee: Tokyo Kogaku Kikai Kabushiki Kaisha, Tokyo, Japan

[21] Appl. No.: 343,512

[22] Filed: Jan. 28, 1982

[30] Foreign Application Priority Data

Jan. 29, 1981 [JP] Japan ............................ 56/11894

[51] Int. Cl.³ .................. G03B 3/10; G03B 29/00; A61B 3/10; H04N 5/26
[52] U.S. Cl. ...................................... 354/25; 354/62; 351/208; 351/211; 358/227
[58] Field of Search .............. 354/25 R, 25 A, 25 P, 354/25 N, 31 F, 62, 79, 23 D; 351/6, 7, 13, 14, 208, 211, 214, 237, 238; 358/225, 227; 356/4, 399, 400; 350/19, 46, 502, 518; 250/201

[56] References Cited

U.S. PATENT DOCUMENTS

| | | | |
|---|---|---|---|
| 3,819,256 | 6/1974 | Bellows et al. | 351/14 X |
| 3,925,793 | 12/1975 | Matsumura et al. | 354/62 |
| 4,187,014 | 2/1980 | Kato et al. | 354/62 |
| 4,277,150 | 7/1981 | Wada et al. | 354/62 X |
| 4,293,198 | 10/1981 | Kohayakawa | 351/13 |

FOREIGN PATENT DOCUMENTS 54-52895 4/1979 Japan .

Primary Examiner—William B. Perkey
Attorney, Agent, or Firm—Brumbaugh, Graves, Donohue & Raymond

[57] ABSTRACT

A focus detecting device for an eye fundus camera including a target having a target pattern comprised of a first slit and a second and third slits disposed in parallel with and at the opposite sides of the first slit. The second and third slits are symmetrical to each other with respect to the first slit. Deflecting prisms are provided to deflect the luminous flux through the first slit in one direction perpendicular to the longitudinal axis of the first slit and the luminous fluxes through the second and third slits in the opposite direction. The slit pattern is convenient for automatic focus adjustment.

7 Claims, 12 Drawing Figures

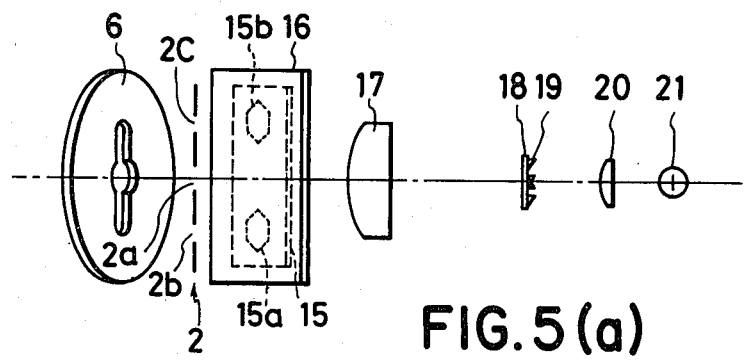
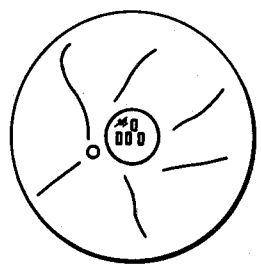
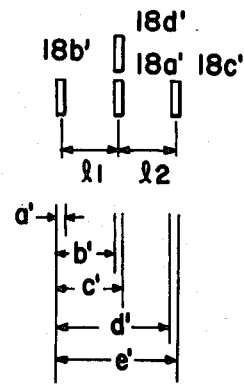
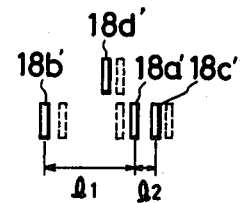
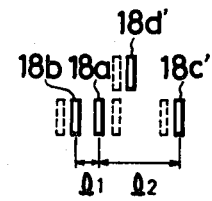

FOCUS DETECTING DEVICE FOR OPTHALMOLOGIC INSTRUMENTS

The present invention relates to a focus detecting device for ophthalmologic instruments.

Conventionally, in order for facilitating focusing an eye fundus camera on the fundus of a patient's eye, an image of a target is optically projected on the eye fundus. The U.S. Pat. Nos. 3,925,793 and 4,187,014 disclose a technique for detecting a focus condition of the projected target image and performing adjustments for obtaining a desired focus condition on the eye fundus. In the above-mentioned patents, the target comprises a single slit opening and a pair of deflecting prisms which are inclined oppositely to each other and perpendicular to the length of the slit for splitting luminous flux coming from the slit into two parts. The luminous flux coming from the target for detecting a focus condition is projected on the fundus of the patient's eye to produce an image of the target. When the target image is focused on the eye fundus, there is produced an image of a single slit, but when it is out of focus, there is produced two splitted images comprising lower and upper slit images which are offset from each other in the direction perpendicular to the slit direction. By observing the target image projected on the fundus, adjustments may be made so that the slit image is focused on the eye fundus to thereby focus the optical system of the eye fundus camera on the eye fundus. According to the above-mentioned patents, focus adjustment is carried out manually by the operator who is observing the target image projected on the eye fundus.

Art to detect a focus condition of the target image photoelectrically and to carry out focus adjustment automatically from signals thus detected is proposed by Japanese Patent Application Disclosure No. 54-52895. In the proposal, use is made of a similar focus detecting target as used in the above-mentioned U.S. Pat. Nos. 3,925,793 and 4,187,014, and a focus condition on the eye fundus is detected by measuring the lateral distance between the two slit images formed on the eye fundus under an out-of-focus condition. However, as mentioned above, since the target is comprised of a single slit opening, when the target image is out of focus, the two splitted images of the slit are offset from each other not only in the direction perpendicular to the length of the slit but also in the direction parallel to the length of the slit. Thus, in order to photoelectrically detect the lateral distance between the splitted images, each of the two images must be sensed separately. More precisely, as described in the Patent Application Disclosure No. 54-52895, in case of detecting the lateral positions of the two split images by means of television scanning signals, focus condition is detected only after sensing and comparing picture signals at two scanning lines which are apart by a predetermined distance.

It is therefore an object of the present invention to solve the aforementioned problems of the conventional arrangements and to provide an ophthalmologic instrument having a novel target for focus adjustments. Another object of the present invention is to provide a target which is convenient for detecting a focus condition photoelectrically.

According to the present invention, in order to accomplish the above and other objects, there is provided a focus detecting device for ophthalmologic instruments comprising target means including a target pattern comprised of a first slit having a longitudinal axis and a second and third slits disposed in parallel with and at opposite sides of said first slit, said second and third slits being symmetrical with respect to the first slit, first deflecting means for deflecting a luminous flux through the first slit in one direction perpendicular to the longitudinal axis of the first slit and second deflecting means for deflecting luminous flux through each of the second and third slits in the opposite direction; a target projection system for projecting said target pattern on a patient's eye fundus to produce a target image comprising slit images of the first, second and third slits; an imaging system for forming an image of luminous flux from the target image on the eye fundus; means for photoelectrically detecting distances between the first slit image and the second slit image and between the first slit image and the third slit image to thereby detect a position wherein the target image is focused on the eye fundus.

In a preferable aspect of the present invention, the focus detecting device includes a television system comprising an image pick-up tube which is adapted to convert the image of luminous flux formed by the imaging system to an electric scanning signal and a monitor display device which is adapted to display a target image based on the electric scanning signal. The detecting means then includes means for detecting a focus condition of the target image on the eye fundus from the scanning signal in the television system. The focus detecting device may further include means for extracting feature signals from said scanning signal in a predetermined scanning line, a voltage generating circuit, a timing signal generator for generating from said feature signals timing signals corresponding to a position at which the target image is to be formed, a sample-hold circuit for holding voltages of said voltage generating circuit upon receipt of said timing signals, and an analogue-digital transducer for converting the voltages held by said sample-hold circuit to digital signals, means for determining the distances between the first and second slit images and between the first and third slit images based on said digital signals.

The above and other objects and features of the present invention will become apparent from the following descriptions of a preferred embodiment taking reference to the accompanying drawings, in which:

FIG. 3 is a diagrammatical illustration of a target projecting system;

FIG. 4 shows a target image formed on the eye fundus;

Figure 6:
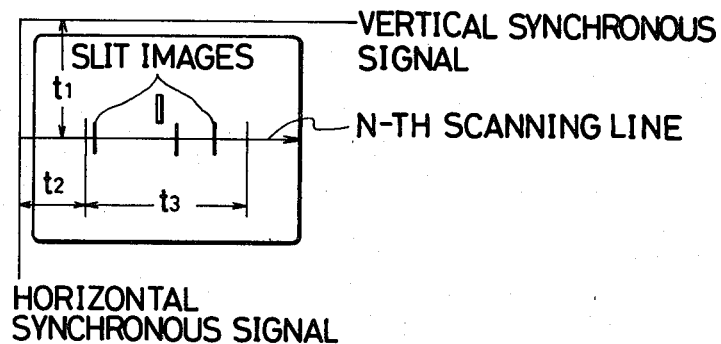
Figure 7:
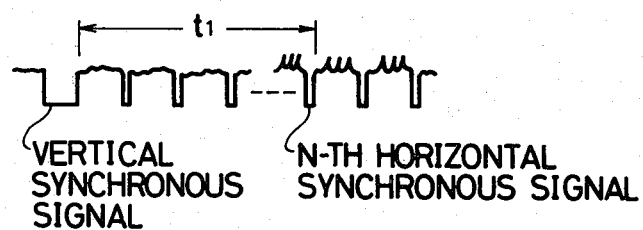
Figure 8:
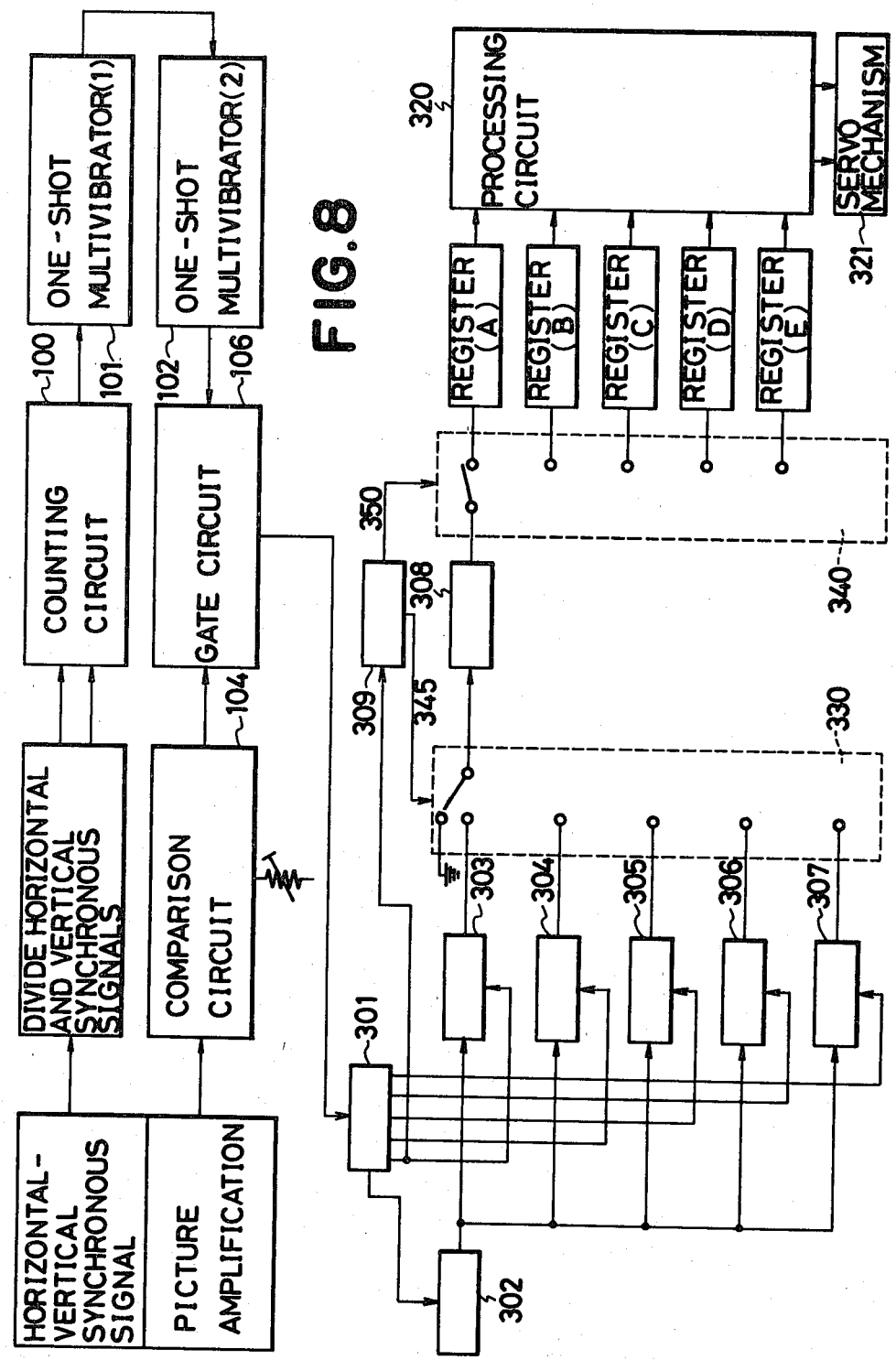
Figure 9:
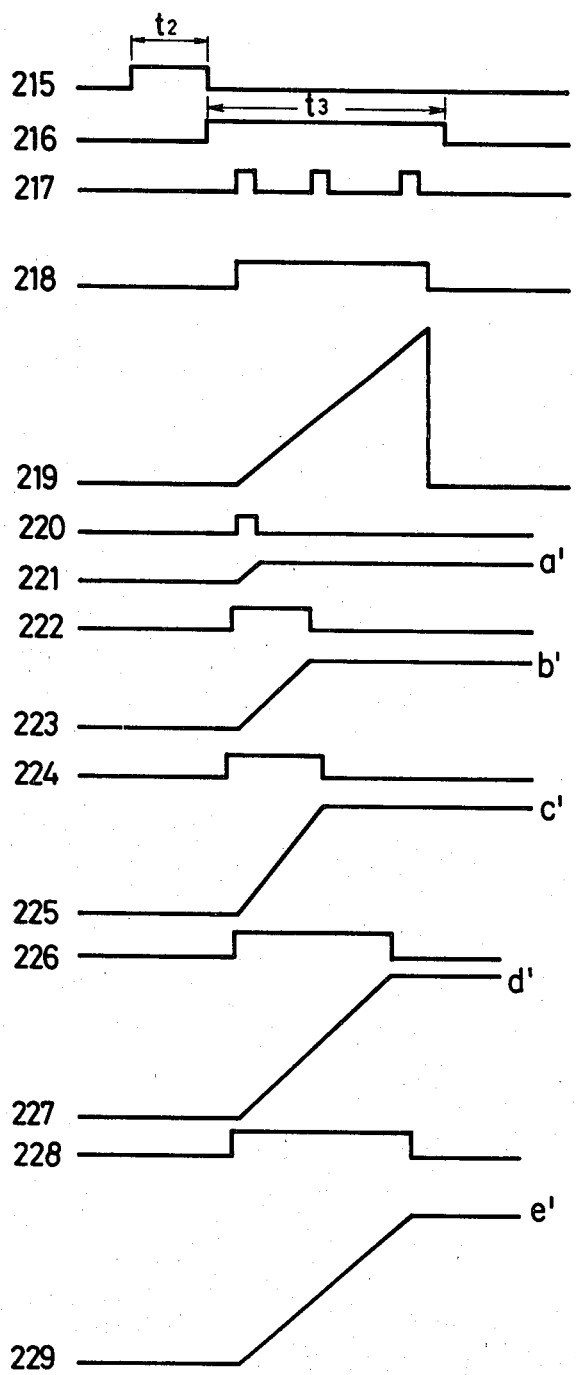

FIGS. 5(a), (b) and (c) show target images in various focus conditions;

FIGS. 6 and 7 are schematic views showing measurement of the distances between the slit images;

FIG. 8 is a block diagram of a control circuit for measuring the distances between the slit images, and FIG. 9 shows waveforms in various components of the circuit shown in FIG. 8.

Figure 1:
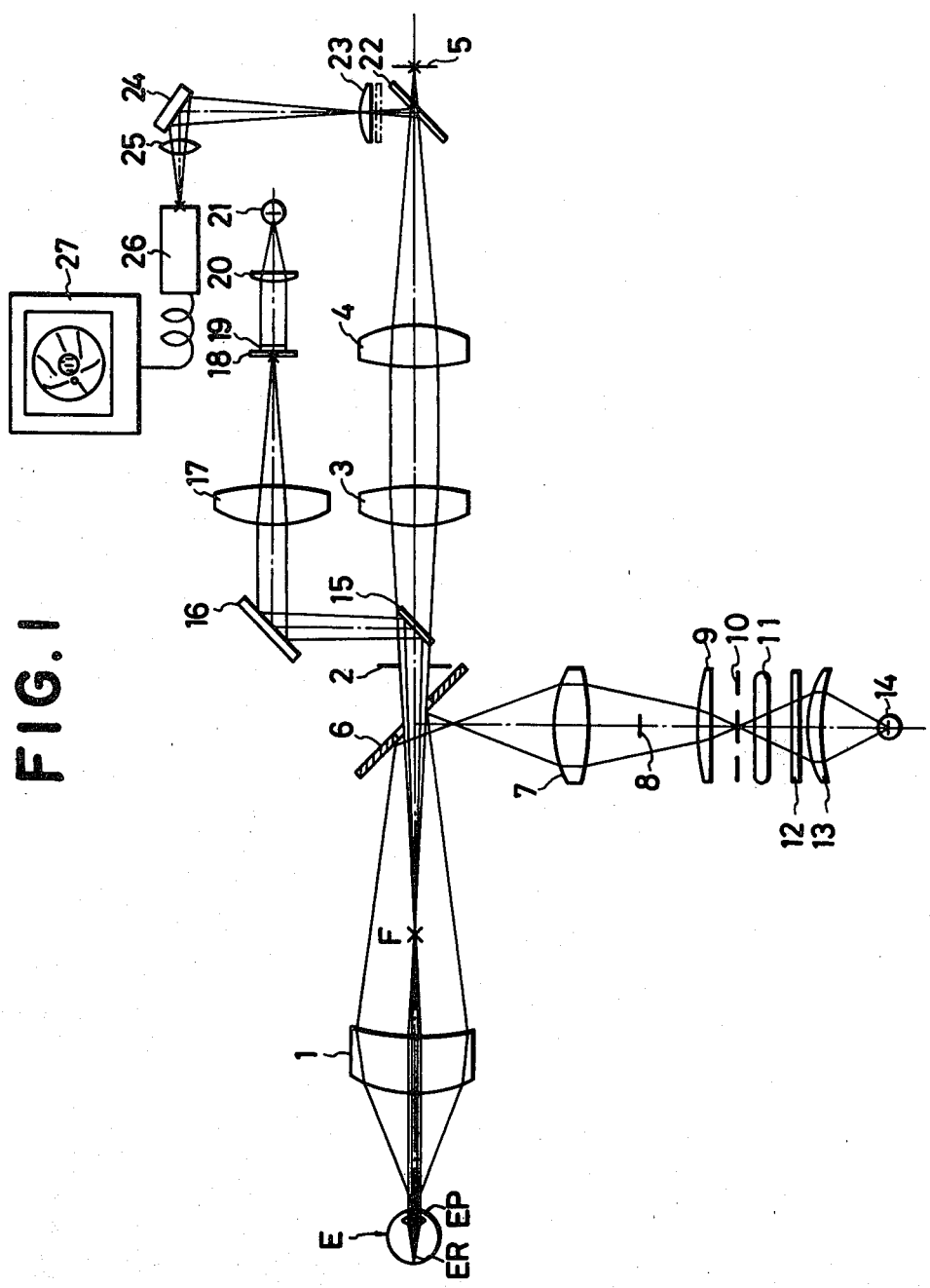
FIG. 1 is a diagrammatical illustration of an optical system of a fundus camera to which the features of the present invention can be embodied.

Referring now to the drawings, particularly to FIG. 1, the eye fundus camera shown therein includes a photographing optical system comprising an objective lens 1 adapted to be positioned against an eye E to be examined, an aperture 2 positioned in conjugate with the pupil $E_p$ of the eye with regard to the objective lens 1, a focussing lens 3, an imaging lens 4 and a photographing film 5, which are arranged so as to form an image of the eye fundus on the film 5. In the optical system, the focussing lens 3 and the imaging lens 4 define an afocal optical system. For observation, there is provided an obliquely disposed reflecting mirror 22 located in front of the film 5, so as to reflect the light beam through the imaging lens 4 substantially perpendicularly. A field lens 23 is provided on a light path reflected by the reflecting mirror 22, and a reflecting mirror 24 and an imaging lens 25 are provided to produce an image on an image pick-up tube 26. The image pick-up tube 26 produces a signal corresponding to the image produced thereon and the signal is transmitted to a infrared monitoring television 27 to form a visual image on the screen of a cathode-ray tube provided therein.

The eye fundus camera further includes an illuminating optical system which comprises an apertured mirror 6 obliquely disposed in the optical path of the photographing optical system in front of the aperture 2, a relay lens 7 provided on the reflecting optical path defined by the apertured mirror 6, a condenser lens 9, a ring slit 10, a flash tube 11, a infrared ray filter 12 which penetrates only an infrared ray, a condenser lens 13, and an ordinary illuminating light source 14. Illuminating light from the light source 14, forming a ring shape, strikes the reflecting surface of the apertured mirror 6 and the light reflected by the mirror 6 illuminates through the objective lens 1 the eye fundus $E_R$.

Figure 2A:
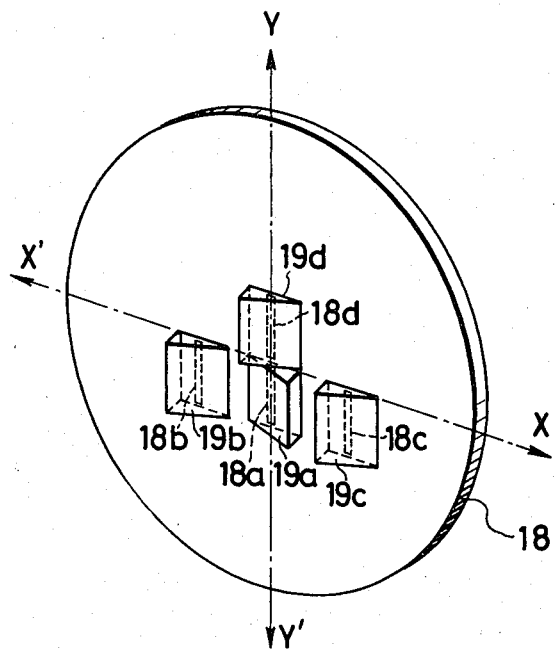
FIG. 2(a) is a perspective view of a target showing a slit pattern in accordance with one embodiment of the present invention.
Figure 2B:
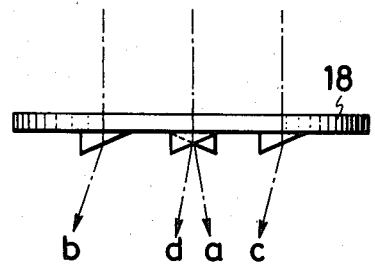
FIG. 2(b) is a top plan view of the target.

For focusing, there is provided a mark projecting system which comprises a reflecting mirror 15 obliquely disposed behind the aperture 2 on the optical path of the photographing optical system, a reflecting mirror 16, a relay lens 17, a target 18, including a pattern in the form of slits and deflecting prisms 19 attached to the slits, a condenser lens 20 and a light source 21 so that the light from the light source 21 passes through the condenser lens 20 to illuminate the slits. As shown in FIG. 2, the target 18 has slits 18a and 18d provided in axial alignment along an axis YY' and slits 18b and 18c provided in parallel with the slits 18a and 18d at the opposite sides of the axis YY' with equal distances therefrom as measured in the direction of an axis XX'. Deflecting prisms 19a, 19b, 19c and 19d are attached to the slits 18a, 18b, 18c and 18d, respectively. As shown in FIG. 2(b), the deflecting prisms 19a, 19b, 19c and 19d serve to deflect the light passing through the associated slits in the directions shown by arrows a, b, c and d, respectively, within the plane including the XX' axis. The light beams which have passed through the slits are passed through the relay lens 17, the reflecting mirrors 16 and 15, the aperture 2 and the aperture portion of the apertured mirror 6 to be focused at a position F which is conjugate with the film 5 with respect to the lenses 3 and 4, and projected through the objective lens 1 to the eye E.

As mentioned above, in order to reflect the light beams which have passed through the slits and deflected by the prisms toward the objective lens 1, the reflecting mirror 15 includes a pair of reflecting surfaces 15a and 15b which are disposed symmetrically with respect to the optical axis of the photographing optical system, as shown in FIG. 3. Therefore, the reflecting mirror 15 does not provide any obstruction to the effective luminous flux of the photographing optical system which has been reflected at the eye fundus $E_R$ and is advancing to the film 5. In order to pass the luminous flux passing along the optical axis of the photographing optical system and the luminous flux which has passed through the slits, the aperture 2 has a central aperture 2a for passing the photographing luminous flux and apertures 2b and 2c at both sides of the central aperture 2a for passing the luminous flux which has passed through the slits. Furthermore, the apertured mirror 6 has an elongated aperture so as to pass the light beams which have passed through the slits.

In order to obtain a higher contrast of the projected slit images on the eye fundus $E_R$, it is desirable to block the background illumination where the slit pattern is projected. For the purpose, in this embodiment, a blocking plate 8 is retractably positioned in the illuminating system at a position conjugate with the eye fundus $E_R$. The plate 8 has an area that can adequately cover the slit images.

In the optical system shown in FIGS. 1 and 2, the focussing lens 3 is moved along the optical axis as a unit with the relay lens 17, the target 18, the deflecting prism 19, the condenser lens 20 and the infrared light source 21 to carry out a focus adjustment. In this instance, the focusing condition of the eye fundus image on the photographing film 5 can be known from the focusing condition of the slit images on the eye fundus $E_R$.

With the structure as mentioned above, the slit images are overlapped with the eye fundus image on the monitoring television 27 as shown in FIG. 4. The relationship between the focus condition of the eye fundus image and the slit images is shown in FIG. 5. FIG. 5(a) shows the slit pattern image in accurate focus and FIGS. 5(b) and (c) show the slit pattern images under out of focus. As the slit pattern image plane is displaced along the optical axis with respect to the eye fundus, the slit image 18a' is displaced in the direction opposite to the direction of the displacement of the slit images 18b' and 18c'. Under an accurate focus condition, the distance $l_1$ between the slit image 18b' and 18a' becomes equal with the distance $l_2$ between the slit images 18a' and 18c'. The slit image 18d', which is in vertical alignment with the slit image 18a' at a focus condition, is provided so that an operator can easily recognize a focus condition. The distances $l_1$ and $l_2$ are electrically detected and depending on whether the value $(l_1-l_2)$ is positive or negative, the direction of the displacement of the focusing lens 3 is determined. When the distance $l_1$ is equal to the distance $l_2$, it is judged that a satisfactory focus condition is established. In the illustrated embodiment, focusing condition can also be judged by observation. More precisely, the accurate focus can be detected by the longitudinal alignment of the slit images 18a' and 18b'. Thus, the operator can confirm the accurate focusing condition not only with the above-mentioned automatic detector but also with his own eyes so that it is possible to readily find any trouble which may occur in the automatic focus detecting device.

As means to detect the above-mentioned distances $l_1$ and $l_2$, any of various known techniques can be used such as a photodiode array having a plurality of small light receiving surfaces arranged in a row, or an array of charge coupled elements. Alternatively, use may be made of a slit aperture having a photoelectric detector to scan the plane where the slit images are to be produced. In the present embodiment, the automatic focusing can be achieved by detecting the slit image positions by the television picture scanning signals. FIGS. 6 and 7 show an example of the slit pattern image on the monitoring television and the timing in which the picture signals are picked up. As shown in FIGS. 6 and 7, starting from the vertical synchronizing signal, an $n^{th}$ scanning signal is picked up after a time $t_1$ from the vertical synchronizing signal, and then starting from the horizontal synchronizing signal on the $n^{th}$ scanning line, signals are picked up for a length of time $t_3$ from a time $t_2$ after the horizontal synchronizing signal. Referring to FIG. 8 which shows a block diagram for signal processing circuit to carry out the automatic focus setting by signals from the monitoring television and to FIG. 9 which shows signal waveforms, it will be noted that composite electric signals are divided to horizontal-vertical synchronous signals and picture signals. The former signals are further divided to horizontal synchronous signals and vertical synchronous signals and applied to a counting circuit 100. The counting circuit 100, by counting the $n^{th}$ horizontal synchronous signals, selects the $n^{th}$ scanning signal at the time $t_1$ from the vertical synchronous signal and generates a pulse. At this timing, a first one-shot multivibrator 101 and a second one-shot multivibrator 102 generate signals 215 and 216 respectively. A vertical synchronous signal resets the counting circuit 100 every one field. More precisely, the one shot multivibrator 102 generates a gate signal 216 having a pulse width corresponding to a length of time $t_3$ starting at the time $t_2$ from the $n^{th}$ scanning signal. The gate signal 216 is supplied to a gate circuit 106 and allows the gate circuit to pass signals during the time $t_3$. On the other hand, the picture signal is converted to H (high) and L (low) binary signal, which is shown as signal 217 in FIG. 9, by a comparison circuit 104, and applied to a gate circuit 106 which picks-up the picture signal 217 converted to a binary signal at $n^{th}$ scanning line. The picture signal 217 passes through the gate circuit 106 to a timing signal generating circuit. The numeral 301 designates a timing signal generating circuit which generates timing signals 218, 220, 222, 224, 226 and 228. The timing signal 218 is supplied to a voltage generating circuit 302, and timing signals 220, 222, 224, 226 and 228 are supplied to sample-hold circuits 303, 304, 305, 306 and 307, respectively. The voltage generating circuit 302 generates a voltage 219 having good linearity. Supplied with the above-mentioned timing signals, the sample-hold circuits 303, 304, 305, 306 and 307 convert the voltage 219 to the voltages 221, 223, 225, 227 and 229 to obtain voltages of an electric quantity necessary for sampling during the period wherein an H (high) signal is produced.

The sample-hold circuits 303 to 307 are connected to a circuit selector 330. This circuit selector 330 is controlled by the output signals of a timing signal generating circuit 309 for circuit selection and selects sequentially an appropriate sample-hold circuit which is then connected to an A/D transducer 308. The output of the A/D transducer 308 is applied to a circuit selector 340. The circuit selector 340 is controlled by the output signals of the timing signal generating circuit 309 for circuit selection and selects registers A through E corresponding to the circuit selector 330. Consequently, the registers A through E memorize signals digitalized by the A/D transducer 308. An processing circuit 320 is connected with the registers A through E and calculates the distances $l_1$ and $L_2$ between the three slit images and gives signals regarding to the quantity and direction of adjustment to a servo system 321 until two distances become equal. Supposing that the digital quantities memorized by the registers A through E are a, b, c, d, and e, respectively, the distance $l_1$ in FIG. 5 is calculated by the equation $l_1 = a/2 + (b-a) + (c-b)/2 = (b - a + c)/2$ and $l_2$ is calculated by the equation $l_2 = (c-b)/2 + (d-c) + (e-d)/2 = (d-c+e-b)/2$. The digital quantities a, b, c, d, and e correspond to the distances a', b', c', d', and e', respectively, shown in FIG. 5. Where $\Delta l = l_1 - l_2$ is the quantity of adjustment and the direction of adjustment is judged whether the value $l_1 - l_2$ is positive or negative. The servo system 321 moves the focusing lens 3 with the relay lens 17, the slit mark 17, the deflecting prism assembly 19, the condenser lens 20 and the light source 21 of the target projecting system as a unit along the optical axis to carry out the automatic focus adjustment of the eye fundus image on the film 5 by observing the focusing condition of the slit pattern image on the eye fundus.

As a means to convert the feature signal picked up from the monitoring television 27 to a position signal, it has been known to measure the time when the feature signal is generated. In this case, an output is made as a pulse train in a digital mode counted by a clock pulse provided separately. This method, however, has a problem, in that accuracy depends on the frequency of the clock pulse. To attain high accuracy, a high frequency clock pulse must be used and this will necessitate the use of circuits with excellent high frequency characteristics. On the other hand, in the present embodiment, the feature signal is converted to a sampling pulse, and necessary voltage is obtained at the sample-hold circuit where a quantity of electricity required at that time is converted to an analogue value. The voltage is digitalized by the analogues-digital transducer. In this case, adoption of a high bit analogue-digital transducer makes it possible to attain high precision.

The invention has thus been shown and described with reference to a specific embodiment, however, it should be noted that the invention is in no way limited to the details of the illustrated arrangements but changes and modifications may be made without departing from the scope of the appended claims.

We claim:

1. A focus detecting device for ophthalmologic instruments comprising target means including a target pattern comprised of a first slit having a longitudinal axis and a second and third slits disposed in parallel with and at the opposite sides of said first slit, said second and third slits being symmetrical with respect to the first slit, first deflecting means for deflecting a luminous flux through the first slit in one direction perpendicular to the longitudinal axis of the first slit and second deflecting means for deflecting luminous flux through each of the second and third slits in the opposite direction; a target projection system for projecting said target pattern on a patient's eye fundus to produce a target image comprising slit images of the first, second and third slits; an imaging system for forming an image of luminous flux from the target image on the eye fundus; means for photoelectrically detecting distances between the first slit image and the second slit image and between the first slit image and the third slit image to thereby detect a position wherein the target image is focused on the eye fundus.

2. A focus detecting device according to claim 1, which further includes a television system comprising an image pick-up tube for converting said image of luminous flux formed by said imaging system to an electric scanning signal and a monitor display device for displaying a target image based on said electric scanning signal, said detecting means including means for detecting a focus condition of the target image on the eye fundus from said scanning signal in said television system.

3. A focus detecting device according to claim 2, in which said focus detecting means includes means for extracting feature signals from said scanning signal in a predetermined scanning line, a voltage generating circuit, a timing signal generator for generating from said feature signals timing signals corresponding to a position at which the target image is to be formed, a sample-hold circuit for holding voltages of said voltage generating circuit upon receipt of said timing signals, and an analogue-digital transducer for converting the voltages held by said sample-hold circuit to digital signals, and means for determining the distances between the first and second slit images and between the first and third slit images based on said digital signals.

4. A focus detecting device according to claim 1 in which said target pattern includes a fourth slit which is in a longitudinal alignment with the first slit, said fourth slit being associated with third deflecting means for deflecting a luminous flux through the fourth slit in a direction opposite to said one direction.

5. A focus detecting device according to claim 4 in which said fourth slit is formed as a longitudinal extension of the first slit.

6. A focus detecting device according to claim 1 in which said first and second deflecting means are prisms having surfaces inclined perpendicularly to said longitudinal axis of the first slit.

7. A focus detecting device according to claim 4 in which said third deflecting means is a prism.

* * * * *